United States Patent
Duval

(10) Patent No.: US 6,677,446 B2
(45) Date of Patent: Jan. 13, 2004

(54) CROSS-LINKED POLYMERS BASED ON BIS-SILANE, BIS-THIOETHER, BIS-SULPHOXIDE, BIS-SULPHONE AND BUTANE-DI-YL DERIVATIVES OF POLYSACCHARIDES AN OLIGOSACCHARIDES, AND THEIR SHAPING AS SUPPORT MATERIALS

(75) Inventor: Raphaël Duval, Notre Dame de Gravenchon (FR)

(73) Assignees: Institut Francais du Petrole, Rueil-Malmaison (FR); Chiralsep S.a.r.L., La Frenaye (FR)

( * ) Notice: Subject to any disclaimer, the term of this patent is extended or adjusted under 35 U.S.C. 154(b) by 103 days.

(21) Appl. No.: 09/838,284

(22) Filed: Apr. 20, 2001

(65) Prior Publication Data

US 2001/0029282 A1 Oct. 11, 2001

Related U.S. Application Data

(62) Division of application No. 09/394,905, filed on Sep. 13, 1999.

(30) Foreign Application Priority Data

Sep. 11, 1998 (FR) .............................. 98 11376

(51) Int. Cl.[7] .............................................. C08B 37/00
(52) U.S. Cl. ............... 536/55.1; 536/123.1; 536/123.12
(58) Field of Search .......................... 536/123.1, 123.12, 536/55.1

(56) References Cited

U.S. PATENT DOCUMENTS 5,772,876 A  6/1998  Murakami

FOREIGN PATENT DOCUMENTS

| EP | 0 168 363 | | 1/1986 |
| EP | 0 738 284 B1 | * | 1/1996 |
| FR | 1 307 274 | | 2/1963 |
| WO | WO 95/18833 | | 7/1995 |

OTHER PUBLICATIONS

Minguillon, C. et al. "Bonded cellulose–derived high performance liquid chromatography . . . " J. Chromatog. A, vol. 728, pp. 415–422.
Olivers, L. et al. "Chiral chromatographic discrimination ability . . . " J. Liq. Chromatog. vol. 18, No. 8, pp. 1521–1532.
Franco, P. et al. "3,5–Dimethylphenylcarbamates of amylose, chitosan, and cellulose . . . " J. Chromatog. A, vol. 796, pp. 265–272.
Okamoto, Y. et al. "Useful chiral packing materials for high–performance liquid chromatographic resolution of enantiomers" J. Am. Chem. Soc., vol. 107, No. 18, pp. 5357–5359.
Giuliana C. Tesoro, "Cross–Linking of Cellulose with Polyfunctional Sulfones under Anhydrous Conditions", vol. 32, No. 3, Mar. 1, 1962, pp. 189–190.

* cited by examiner

Primary Examiner—Samuel Barts
Assistant Examiner—Michael C Henry
(74) Attorney, Agent, or Firm—Millen, White, Zelano & Branigan, P.C.

(57) ABSTRACT

There are described novel cross-linked polymers based on bis-silane, bis-thioether, bis-sulphoxide, bis-sulphone and butane-di-yl derivatives of polysaccharides and oligosaccharides, their shaping as support materials useful for the separation or preparation of enantiomers; a process for preparing the said cross-linked polymer compounds, a process for preparing balls of support materials containing the said cross-linked polymer compounds; a method of obtaining balls of support materials useful in chromatography or in organic synthesis; and the use of the said support materials containing the cross-linked polymer compounds in separation or in preparation of enantiomers, through employment in chromatography or organic synthesis processes in a heterogeneous medium; and the use of the said cross-linked polymer compounds in the form of membranes in processes using percolation through membranes for the separation or the preparation of enantiomers.

8 Claims, 6 Drawing Sheets

2,2,2-Trifluoro-1-(9-anthryl)ethanol
(non racemic)

INDAPAMIDE 2,2,2-Trifluoro-1-(9-anthryl)ethanol
(non racemic)

$k'_1 = 4.2$
$k'_2 = 6.3$
$\alpha = 1.5$

CROSS-LINKED POLYMERS BASED ON BIS-SILANE, BIS-THIOETHER, BIS-SULPHOXIDE, BIS-SULPHONE AND BUTANE-DI-YL DERIVATIVES OF POLYSACCHARIDES AN OLIGOSACCHARIDES, AND THEIR SHAPING AS SUPPORT MATERIALS

This is a division, of application Ser. No. 09/394,905 filed Sep.13, 1999.

The invention relates to novel cross-linked polymers based on bis-silane, bis-thioether, bis-sulphoxide, bis-sulphone and butane-di-yl derivatives of polysaccharides and oligosaccharides, and their shaping as support materials useful for the separation or the preparation of enantiomers.

The invention also relates to a process for preparing the said cross-linked polymer compounds and a process for preparing balls of support materials containing the said cross-linked polymer compounds.

The invention also relates to a method of obtaining balls of support materials useful in chromatography or in organic synthesis.

The invention also relates to the use of the said support materials containing the cross-linked polymer compounds in the separation or in the preparation of enantiomers, through employment in chromatography or organic synthesis processes in a heterogeneous medium.

The invention also relates to the use of the said cross-linked polymer compounds in the form of membranes in processes using percolation through membranes for the separation or the preparation of enantiomers.

The separation of enantiomers has been an expanding field for some twenty years, at both the preparation and analysis level. This is true in particular of pharmacy applications, where legislation requires a separate study of the optical isomers of any compound included in the composition of a medicament. Substituted polysaccharides have been the subject of numerous studies, and celluloses deposited physically on a silica gel support are marketed. However, such compounds have the disadvantage of being most often soluble in organic polar solvents, which singularly limits their use.

Recent solutions have been provided to the problem of solubil-ization, by establishing covalent bonds between the substituted polysaccharide and the support. Kimata et al. published their results (Analytical Methods and Instrumentation, Vol. 1, 23–29 (1993)) on a chiral stationary phase based on cellulose-tris-2,3,6-(4-vinyl benzoate) deposited on silica gel then polymerized on the support.

The chromatographic data obtained with two racemic test mixtures are as follows:

|  | Deposited support | | Deposited and polymerized support | |
| --- | --- | --- | --- | --- |
|  | Stilbene oxide | 1-(1-naphthyl ethanol) | Stilbene oxide | 1-(1-naphthyl ethanol) |
| k'1 | 1.08 | 2.15 | 1.04 | 1.47 |
| k'2 | 1.66 | 2.84 | 1.44 | 1.80 |
| α | 1.54 | 1.32 | 1.39 | 1.22 |
| $R_s$ | 3.63 | 2.34 | 3.82 | 1.44 | where k'1 and k'2 are the capacity factors, that is to say if i=1 or 2, $k'_i = (t_{Ri} - t_o)/t_o$.

$t_{Ri}$ being the retention time of the compound i and $t_o$ the dead time;

α is the selectivity factor: $\alpha = (t_{R2} - t_o)/(t_{R1} - t_o) = k'2/k'1$ $R_s$ is the resolution factor:

$$R_s = \frac{1}{4}\left(\frac{(\alpha-1)}{(\alpha)}\right)\left(\frac{(k'2)}{(1+k'2)}\right)(N)^{\frac{1}{2}}$$

N being the number of plates determined on the basis of chromatographic values measured on the chromatogram.

A systematic decline in the obtained selectivity factors can be seen between the deposited support and the deposited and polymerized support: 10% less on trans-stilbene oxide (α changes from 1.54 to 1.39) and 7.5% less for 1-(1-naphthyl)ethanol (α changes from 1.32 to 1.22).

This phenomenon could be explained by a partial solubility of the polymerized support because of an incomplete polymerization due to a low reactivity of the vinyl benzoate group under the reaction conditions employed.

On the other hand, Kimata et al. offer no example of separation in a pure polar solvent (patent or publication).

Okamoto et al. have described (EP-B-0 155 637) polymers chemically bound to silica gel. They describe in particular the grafting of cellulose tris-2,3,6-phenyl carbamate onto silica gel via a tritylated intermediate then the realization of the covalent bond, between the silica gel and the partially derived polysaccharide carbamate, by action of a diisocyanate.

The results of the elemental analyses carried out at various synthesis stages are as follows (EP-B-0 155 637, page 8 to page 9, line 33).

|  | C % | H % | N % |
| --- | --- | --- | --- |
| 1. Cellulose trityl deposited on silica | 15.40 | 1.23 | 0.09 |
| 2. Detriylated cellulose deposited on silica | 3.61 | 0.60 | — |
| 3. Cellulose bound to the silica by toluene 2,4-diisocyanate | — | — | — |
| 4. Phenyl carbamate cellulose bound to the silica and washed with THF/chloroform | 3.23 | 0.27 | 0.45 |

The drop in the rate of grafting between the cellulose deposited on silica (2) and the cellulose phenyl carbamate bound to the silica (4) is substantial knowing that the rate of (4) calculated according to (2) is of the order of 14% carbon. The loss of hydrocarbon groups can thus be estimated at 80% from the realization of the covalent bond, between the cellulose and the silica, by the diisocyanate arm followed by the derivation of the OHs with phenyl isocyanate and the final washing with chloroform.

No example of separation in polar solvents is given for the support obtained.

Okamoto et al. have described (JP-A-06-206 893) an oligosaccharide chemically bound to silica gel via an amine-reduced imine function. The amylose is then regenerated by the chimioenzymatic route from this oligosaccharide. The available hydroxyl functions are then derived as carbamate functions. No example of separation in a pure polar solvent is given.

On the other hand, it is beneficial to work with a substantial column overload for preparatory applications. The possibility of using 100% of the chiral material in the form of balls of pure polymer of substituted polysaccharides, instead of depositing them physically on a support, has proved effective in increasing the mass yields of preparatory chiral chromatography processes. Thus Patents EP-B-348 352, and EP-B-316 270 and Application WO-A-96127 639 relate to the realization of cellulose balls for the separation of optical isomers.

However, the pure polymer balls are soluble in polar solvents such as halogenated solvents, tetrahydrofuran, dioxan, etc. It is thus impossible to use these pure solvents or mixtures with high proportions of these latter to realize separations of isomers.

In order to overcome this drawback, Francotte et al. have described the polymerization by radiation of derived polysaccharides (WO-A-96/27 615).

However, the rate of polymerization seems difficult to control in such a process, cross-linking by photochemical process preferentially occurring at the surface of the polymer ball, the rays being unable to penetrate inside the ball. No example of separation is given in a pure polymer.

Francotte et al. have also described in International Application WO-A-97/04 011 the chemical cross-linking of carbamates and esters of polysaccharides not containing a polymerizable group. According to the author, cross-linking took place in the presence of a radical polymerization initiator. The reaction mechanism and the structure of the products obtained are not described. No example of separation in a pure polar solvent is given.

Lange at al. have described (U.S. Pat. No. 5,274,167) the polymerization of optically active derivatives of methacrylic acid, the structure of the support not being explained. No example of separation in a pure polar solvent is given.

Minguillon et al. have described the synthesis of partially derived cellulose carbamates with an undecenoyl chloride. However, the structure of the support is not explained (J. of Chromatog. A 728 (1996), 407–414 and 415–422).

Oliveros et al. (WO-A-95/18 833) describe polysaccharides derivatives containing an ethylene radical and deposited on a silica gel support containing vinyl groups then polymerized. No example of separation is given with a pure polar solvent.

The invention relates to novel polymer compounds cross-linked through the agency of covalent bonds between separate chains of an osidic linkage of derivatives of polysaccharides or oligosaccharides, the said covalent bonds containing butane di-yl, bis-silane, bis-thioether, bis-sulphoxide or bis-sulphone functions.

These novel cross-linked polymer compounds are insoluble in polar organic solvents such as for example tetrahydrofuran, 1,4-dioxan, chloroform, dichloromethane, dichloroethane, isopropyl chloride, chlorobutane, acetone, methyl ethyl ketone, acetonitrile, nitro-methane, alcohols such as methanol and ethanol, and esters such as ethyl or butyl acetate.

Figure 1:
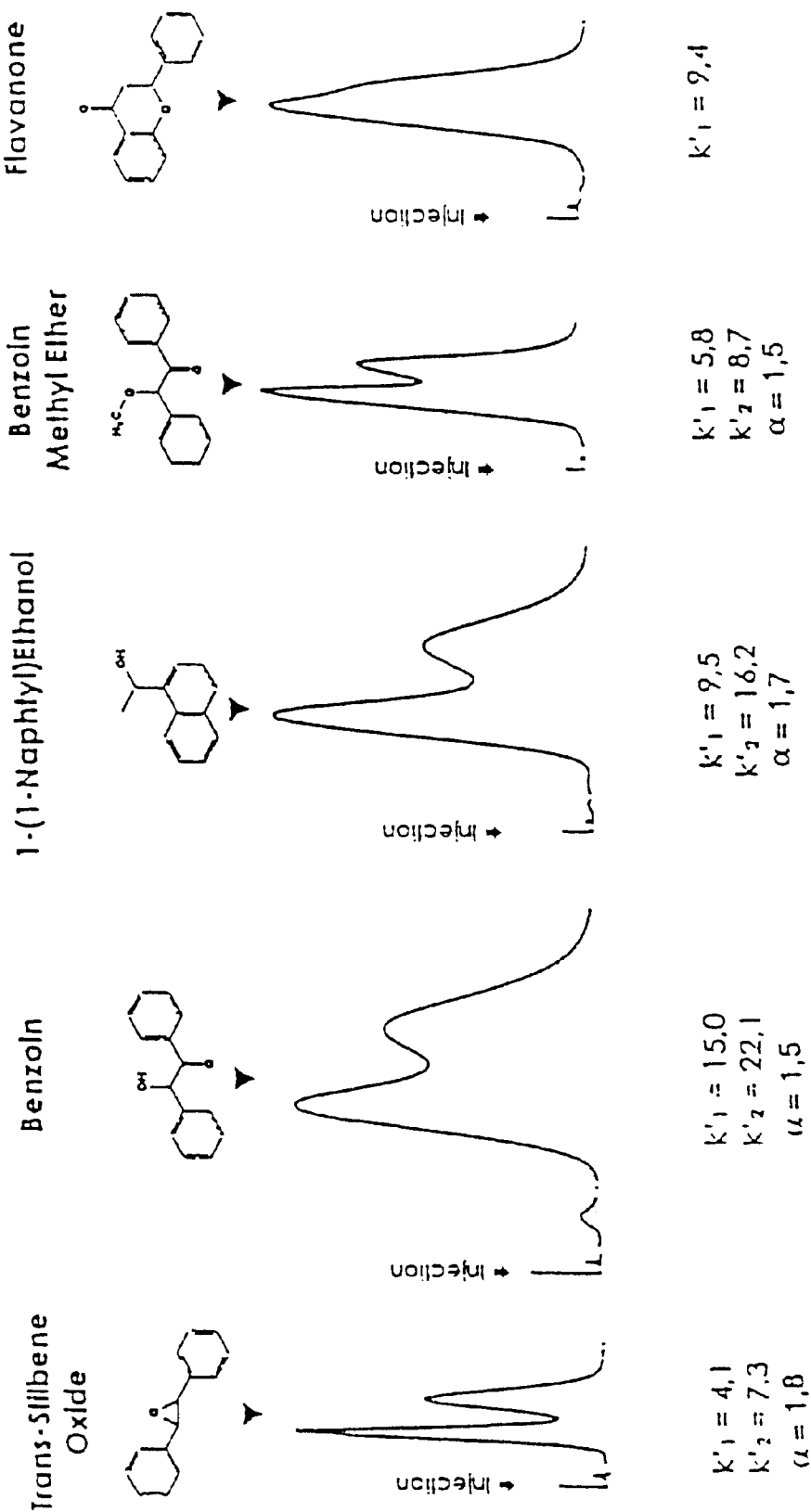
FIG. 1 depicts results of a first rest carried our in a 90/10 heptane/isopropanol mixture.

Balls of support materials containing the said cross-linked polymer compounds are useful for the separation of enantiomers by liquid or supercritical chromatography. Surprisingly, a heat treatment, up to 80° C., in polar organic solvents, of the said support materials does not alter their chiral discrimination property when they are used in enantioselective separation processes.

This property is particularly useful in the pharmaceutical industry, as the possibility of using eluent mixtures consisting of polar organic solvents, pure or in a high percentage, in preparatory chiral chromatography for the industrial separation of racemic mixtures for example, allows a very appreciable increase in the concentration of the solutes as the chromatographic process unfolds. Solvent consumption is thereby reduced and separation productivity correspondingly improved.

The cross-linked polymer compounds are characterized in that they contain a radical of general formula (I) or (II):

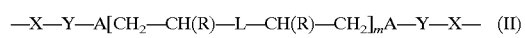

in which X represents an oxygen atom or the group —NH, m is an integer other than zero equal at most to 5, R represents a hydrogen atom or a substituted or non-substituted, linear or branched alkyl radical having from 1 to 8 carbon atoms, Y represents a single bond, —NH—CO— group, —NH—CS— group or —CO— group, A represents a single bond, a linear or branched alkylene radical having from 1 to 21 carbon atoms, an arylene radical having from 6 to 18 carbon atoms or an aralkylene radical having from 7 to 40 carbon atoms, L represents a bis-thioether radical, of general formula (IIIa), bis-sulphoxide radical of general formula (IIIb), or bis-sulphone radical, of general formula (IIIc), or a bis-silane radical of general formula (IV):

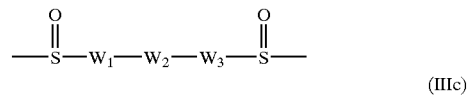

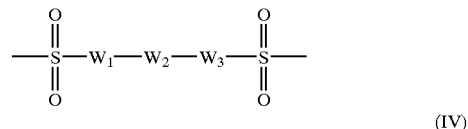

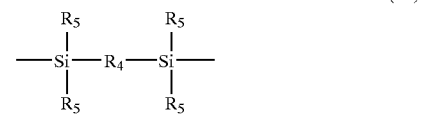

where S represents a sulphur atom, O an oxygen atom and Si a silicon atom; and where $W_1$ and $W_3$, identical or different, each represent:
a linear or branched alkylene radical having from 1 to 21 carbon atoms, an arylene radical having from 6 to 18 carbon atoms, or an aralkylene radical having from 7 to 40 carbon atoms, $W_2$ represents a single bond, $W_1$ an oxygen atom, a sulphur atom or a symmetrical diester of formula

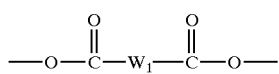

(V)

$R_5$ represents a linear or branched alkyl radical having from 1 to 5 carbon atoms or hydrogen, and $R_4$ represents the radical

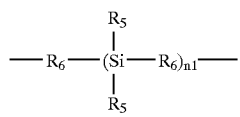

(VI)

where $R_6$ is $(CH_2)_{n2}$ or oxygen and where n1 varies from 0 to 3000 and n2 from 0 to 10.

Formula (I), which does not contain the radical L, is constructed on a optionally substituted butane-di-yl radical.

The arylene radicals contained respectively in the radicals of the general formulae (I) and (II) may optionally be substituted by one or more atoms or radicals, identical or different, chosen from among halogen atoms, alkyl radicals containing from 1 to 4 carbon atoms, alkoxy radicals containing from 1 to 4 carbon atoms and nitro groups. The arylene radicals contained in the radicals of general formulae (I) and (II) are, preferably, phenylene radicals or naphthylene radicals, optionally substituted by one or more atoms or radicals, identical or different, chosen from among halogen atoms and alkyl radicals containing from 1 to 4 carbon atoms, alkyloxy radicals containing from 1 to 4 carbon atoms and nitro groups.

The cross-linked polymer compounds according to the invention and possessing a radical of general formula (II), and more particularly a bis-thioether type radical of general formula (IIIa), can be transformed into compounds containing the general formulae (IIIb) or (IIIc) by oxidation with the help of oxidizing compounds in order to lead to functionalities of the bis-sulphoxide type or bis-sulphone type.

The transformation of thioether functions into sulphoxide and sulphone functions is known per se and uses several oxidizing agents. Sulphoxides can be obtained from thioethers by using hydrogen peroxide ("Organic Compounds of Bivalent Sulfur" Vol. 2, pp. 64–66, Chemical Publishing Company, New York, 1960) or indobenzene dichloride (Barbieri, J. Chem. Soc. C659, 1968), or sodium metaperiodate (Leonard, J. Org. Chem. 27, 282, 1962) or tertiobutyloxy-chloride (Walling, J. Org. Chem. 32, 1286, 1967) or peracids.

The sulphoxide functions obtained can subsequently be transformed into sulphone functions with the help of potassium permanganate or hydrogen peroxide (Heubert, Chem. Comm. 1036, 1968 and Curci, Tetrahedron Lett., 1749, 1963).

The oxidizing agent used for preference is hydrogen peroxide. The reaction solvent is generally water, an alcohol or an organic solvent miscible with water. The reaction is carried out at a temperature between 10 and 40° C. and the reaction lasts for from 1 to 8 hours.

The cross-linked polymer compounds according to the invention are characterized in that the radicals of general formulae (I) and (II) are bound to osidic chiral units of a linear, branched or cyclic linkage of a polysaccharide or oligosaccharide derivative according to the general formulae (VII) and (VIII) which follow.

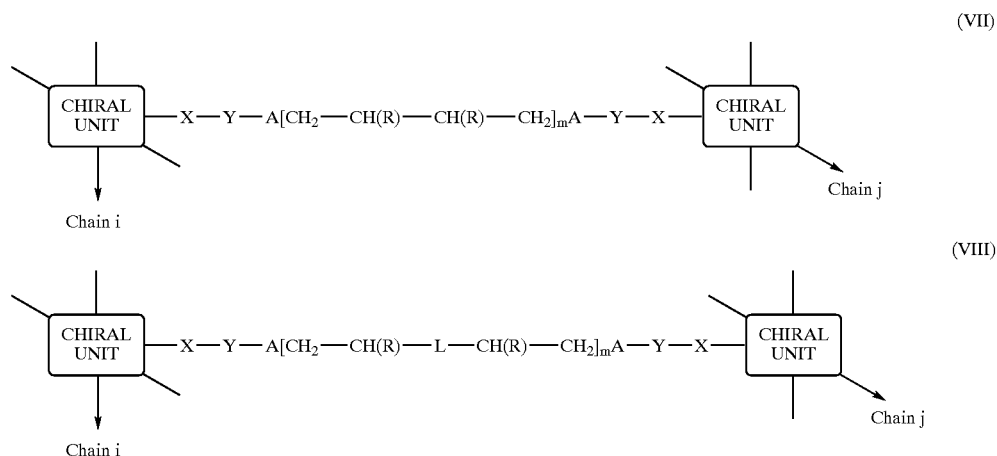

where X, Y, A, R, L and m each have the same meaning as in the general formulae (I) and (II) and in which the "chiral unit" symbol, which will be described by formula (IX), is the osidic chiral unit of a linear, branched or cyclic linkage of a polysaccharide or oligosaccharide derivative, it being understood that "chain i" and "chain j" symbolize the fact that the chiral units at each end of the radicals of formulae (I) and (II) are situated on separate chains or separate linkages of osidic units, within the polysaccharide or the oligosaccharide.

In fact, the recorded insolubility of the cross-linked polymer compounds according to the general formulae (VII) to (VIII) in polar solvents, even at high temperature, can be conferred only by a three-dimensional cross-linking of the polysaccharide, this cross-linking being produced by reaction between the different chains constituting the polysaccharide derivative and leading to a drastic modification of the solubility properties.

Surprisingly, the support materials obtained possess a remarkable stability in all organic solvents, and more particularly in polar organic solvents having a high dissolving power for benzoate and carbamate derivatives of polysaccharides, such as chloroform, acetone, tetrahydrofuran, dioxan or toluene.

Equally surprisingly, these support materials are stable in the solvents mentioned previously up to temperatures that may exceed 80° C. For example, a test for selectivity (α) carried out on indapamide with a support material synthesized according to Example 1 presented below showed that the selectivity factor α (α=1.32 in pure 1,2-dichloroethane at 80° C.) determined according to Example 2, also presented below, is not affected by the passage of some 1000 dead column volumes of the following solvents:

| Solvents | Solvents |
|---|---|
| Diisopropyl ether | Propionitrile |
| Diethyl ether | Benzene |
| Dibutyl ether | Butyl chloride |
| Tert-butyl methyl ether | Chloroheptane |
| Acetaldehyde diethyl acetal | 1,1,1-trichloroethane |
| 1,4-dioxan | Dichloro 1,2-ethane |
| Ethylene glycol dimethyl ether | Trifluoroethanol |
| 2-methoxy ethyl ether | Tert-butyl hydroperoxide |
| Ethyl butyrate | Butyl acetate |
| Methanol | Ethanol |
| Isopropanol | 1-butanol |
| Acetonitrile | Dichloromethane |
| Chloroform | Tetrahydrofuran |
| Ethyl acetate | Nitromethane |
| Acetone | Methyl ethyl ketone |

These properties permit consideration of the use of support materials in processes for the separation or preparation of enantiomers using any type of polar solvent up to temperatures that may exceed 80° C., which seems particularly attractive for industrial applications.

The synthesis of the compounds of general formulae (VII) and (VIII) is carried out in two stages:

synthesis of polysaccharides or oligosaccharides derivatives, activated and bearing ethylene double bonds; and chemical cross-linking of the ethylene double bonds on themselves by a radical mechanism, or by reaction of at least two ethylene double bonds with bifunctional compounds containing bis-thiol or bis-hydrogenosilane functions.

The activated derivatives bearing ethylene double bonds are polysaccharides or oligosaccharides derivatives of the general formulae (Xa) to (Xk):

(Xa)

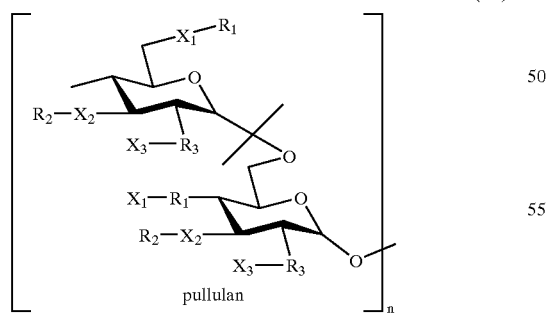

pullulan (Xb)

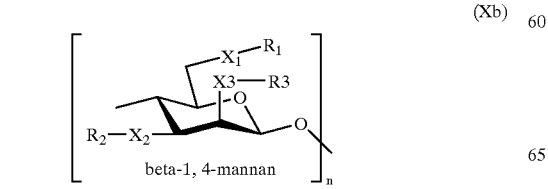

beta-1, 4-mannan (Xc)

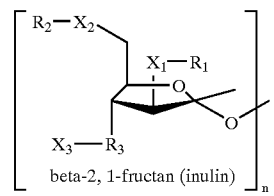

beta-2, 1-fructan (inulin)

(Xd)

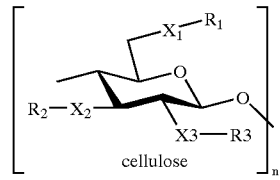

cellulose (Xe)

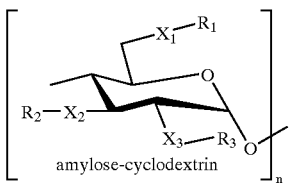

amylose-cyclodextrin (Xf)

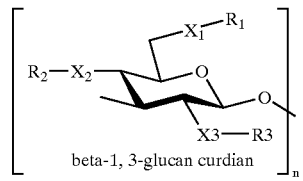

beta-1, 3-glucan curdian (Xg)

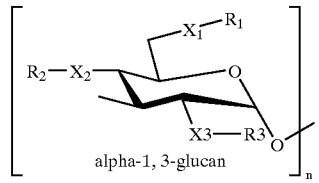

alpha-1, 3-glucan (Xh)

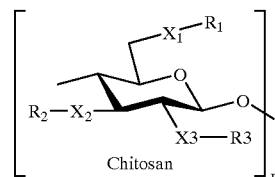

Chitosan (Xi)

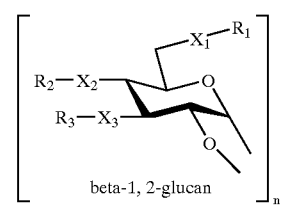

beta-1, 2-glucan

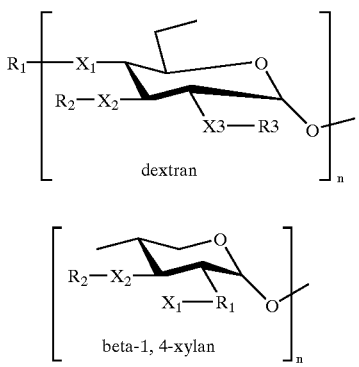

dextran (Xj)

$$\left[\begin{array}{c} R_2-X_2 \\ X_1-R_1 \end{array}\right]_n$$

beta-1,4-xylan (Xk)

In these formulae, a) the symbols $X_1$, $X_2$ and $X_3$, identical or different, each represent an oxygen atom or the group —NH;

b) each of the symbols $R_1$, $R_2$ and $R_3$ independently represents:

an ethylene radical having the general formula:

$$(CH[R]\!=\!CH\!-\!)_{m_1}A\!-\!Y\!- \qquad (XI)$$

in which m1 is an integer other than zero equal at most to 5, R represents a hydrogen atom or a or non-substituted, linear or branched alkyl radical having from 1 to 8 carbon atoms, Y represents a single bond or an —NH—CO— group, an —NH—CS— group or a —CO— group and A represents a single bond, a linear or branched alkylene radical having from 1 to 21 carbon atoms, an arylene radical having from 6 to 18 carbon atoms or an aralkylene radical having from 7 to 40 carbon atoms;

or a radical having the formula $A_2$—$A_1$—$CX_5$— (XII)
in which $X_5$ represents an oxygen sulphur atom, $A_1$ represents a single bond or an —NH— group and $A_2$ represents an aryl radical having from 6 to 24 carbon atoms, an aralkyl radical having from 7 to 36 carbon atoms or an alkylaryl radical having from 7 to 18 carbon atoms;

or a hydrogen atom or an $NO_2$ group;

n being an integer between 5 and 20 000, it being understood that, in each osidic chiral unit (Xa) to (Xk), at least one of the symbols $X_1$, $X_2$ and $X_3$ represents an oxygen atom, and that, in at least one part of the chiral osidic units constituting one of the chains of the polysaccharide derivative, at least one of the symbols $R_1$, $R_2$ and $R_3$ represents a radical of general formula (XI) and at least one of the symbols $R_1$, $R_2$ and $R_3$ represents a radical of general formula (XII).

The arylene or aryl radicals contained respectively in the radicals of general formulae (XI) and (XII) may optionally be substituted by one or more atoms or radicals, identical or different, chosen from among halogen atoms, alkyl radicals containing from 1 to 4 carbon atoms, alkoxy radicals containing from 1 to 4 carbon atoms and nitro groups. The arylene radicals contained in the radicals of general formula (XI) are, preferably, phenylene radicals or naphthylene radicals, optionally substituted by one or more atoms or radicals, identical or different, chosen from among halogen atoms and alkyl radicals containing from 1 to 4 carbon atoms, alkyloxy radicals containing from 1 to 4 carbon atoms and nitro groups. The aryl radicals contained in the radicals of general formula (XII) are, preferably, phenyl radicals or naphthyl radicals, optionally substituted by one or more atoms or radicals, identical or different, chosen from among halogen atoms, alkyl radicals containing from 1 to 4 carbon atoms, alkyloxy radicals containing from 1 to 4 carbon atoms and nitro groups.

Generally, the polysaccharides derivatives according to the invention have a degree of polymerization between 5 and 20 000 and preferably between 10 and 500.

Generally, the polysaccharides derivatives according to the invention contain from 0 to 3, preferably from 0.05 to 2.95 groups of general formula (XI) per osidic unit of general formula (Xa) to (Xk), and from 0 to 3, preferably from 0.05 to 2.95 groups of general formula (XII) per structural unit of general formula (Xa) to (Xk).

Generally, the polysaccharides derivatives according to the invention derive from amylose, cellulose, chitosan or α, β or γ cyclodextrins.

According to the invention, the polysaccharides derivatives can be obtained by action on a non-protected polysaccharide of a compound of general formula:

$$[CH(R)\!=\!CH]_{m_1}A\!-\!Y_1 \qquad (XV)$$

in which R, $m_1$ and A are defined as previously and $Y_1$ represents a halogen atom (chlorine, bromine), an —N=C=O group or —N=C=S group or a —CO—Z— group in which Z represents a halogen atom (chlorine, bromine) in order to introduce an ethylene radical of general formula (XI):

and/or by action of an isocyanate or of an isothiocyanate of general formula:

$$A_2\!-\!A_1\!-\!N\!=\!C\!=\!X_4 \qquad (XVI)$$

in which $A_2$ and $A_1$ are defined as previously and $X_4$ represents an oxygen or sulphur atom or a compound of general formula:

$$A_2\!-\!A_1\!-\!CO\!-\!Z_1 \qquad (XX)$$

in which $A_2$ and $A_1$ are defined as previously and $Z_1$ represents a halogen atom (chlorine, bromine) in order to introduce an ethylene radical of general formula (XII).

According to the invention, the introduction of the radicals of general formula (XI) and/or (XII) takes place under the conditions customarily used for preparing an ether, an ester, an amide, a carbamate, a thiocarbamate, a urea or a thiourea, starting from the corresponding alcohol or amine.

The order of introduction of the reagents of general formula (XV), (XVI) or (XX) influences the enantioselective characteristics of the chiral stationary phases obtained from the thus-modified polysaccharides.

The polysaccharides derivatives according to the invention are obtained from polysaccharides, that is to say having in their structure the repetition of the same chiral osidic unit, as symbolized in the general formulae (Xa) to (Xk).

However, these latter formulae represent only part of the reality, as a polysaccharide is comprised of separate chains of osidic linkages, the number of chains being variable like the length of the osidic linkages represented by the number n of formulae (Xa) to (Xk). Each of the formulae (Xa) to (Xk) represents any one of the linkages of a polysaccharide and constitutes one of the chains among others within the polysaccharide. The cases for example of the cyclomaltohexaose, heptaose and octaose or α, β, γ-cyclodextrins contained in the invention is simpler in so far as n is determined and identical for all the separate (cyclic) linkages.

The polysaccharides derivatives according to the invention are soluble in polar organic solvents such as those mentioned in the table on page 11.

After chemical cross-linking according to the invention, they lead to the novel cross-linked polymers of general formulae (I) and (II) and become totally insoluble in these same solvents.

The polysaccharides derivatives-carrying ethylene double bonds are symbolized by the compounds of general formulae (Xa) to (Xk) containing an ethylene radical of general formula (XI).

where $W_1$, $W_2$ and $W_3$ represent symbols identical to the symbols of the compounds of general formulae (IIIa), (IIIb) or (IIIc).

The preferred bis-thiols are chosen from commercially available compounds such as ethane-dithiol or butane-dithiol. The reaction is conducted at a temperature of 20 to 110° C. in the presence of a free radical initiator, such as benzoyl peroxide for example. The chemical reaction employed is the following:

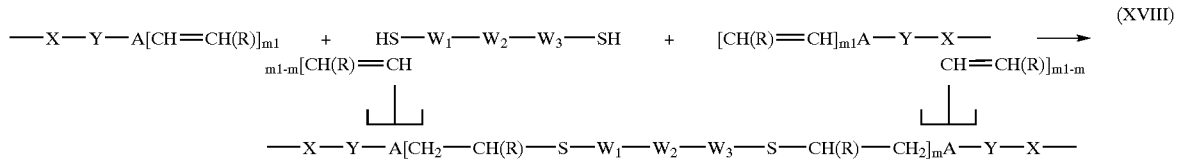

(XVIII)

The ethylene functions of these radicals are reacted on themselves or on compounds containing thiol or hydrogenosilane functions.

The reaction between ethylene double bonds is known per se and can be carried out thanks to an intermediate mechanism for the addition of free radicals (Advanced Organic Chemistry, Jerry March, $2^{nd}$ edition, Chapter 15, MacGraw-Hill Series in Advanced Chemistry). The free radical initiator is generally a peroxide, such as benzoyl peroxide or a diazo compound such as α,α'azo-isobutyronitrile. The reaction is conducted in an organic solvent such as tetrahydrofuran or toluene at temperatures varying from 20 to 200° C. The reaction employed is the following:

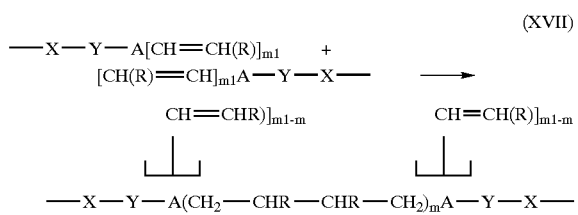

(XVII)

where the symbols X, Y, A, R and m are identical to those described in formulae (I) and (II), and m1 is defined as in formula (XI), and where the radicals of formula (XVII) represent a particular case of compounds containing a radical of general formula (I).

The anti-Markovnikov addition reaction of thiol functions on ethylene double bonds, in the presence of a free radical initiator, which leads to the formation of thioether bonds is known per se.

For example, Rosini and colleagues described the immobilization of cinchona alkaloids via a thioether bond in Tetrahedron Lett. 26, 3361–3364, 1985. More recently, Tambute and colleagues described the immobilization of tyrosine derivatives using the same technique in New J. Chem. 13; 625–637, 1989. Even more recently, Caude and colleagues published the results of their work and showed the advantage of a covalent thioether bond in terms of chemical stability in J. Chromatogr. 550, 357–382, 1991.

The ethylene compounds containing the radicals of general formula (XI) are solubilized in a solvent such as for example toluene, chloroform or tetrahydrofuran, in the presence of a bis-thiol compound of general formula:

$$HS-W_1-W_2-W_3-SH \qquad (XIII)$$

where X, Y, A, R are symbols identical to those described in formula (II); the radicals of general formula (XVIII) represent a particular case of a radical of general formula (II) where L represents a radical of general formula (IIIa), which can be subsequently transformed into a radical of general formula (IIIb) or (IIIc) by oxidation.

The hydrosilylation of ethylene double bonds by hydrogenosilanes is known per se and used to create silicon-carbon bonds. For example, Stuurman, H. W., in Chromatopgraphia [sic], Vol. 25, no. 4, April 1988, pp. 265 to 271, has described the separation of enantiomers through the use of a stationary phase based on hydrosilylated quinine bound to silica gel by a covalent bond.

Polymerization by hydrosilylation is known per se and has been described in J. Chromatogr. 1992, 594, 283–290. This reaction uses hydrosilanes or hydrosiloxanes which can be represented by the following general formula:

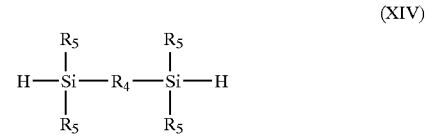

(XIV)

where $R_4$ represents a radical of general formula (VI) defined above and $R_5$ has the same meaning as in the radical of general formula (IV) defined above.

The reaction is the following:

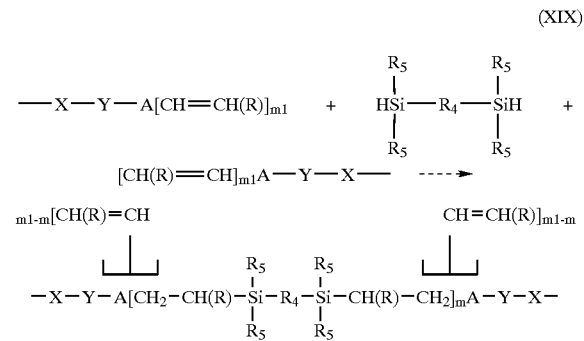

(XIX)

The radicals of general formula (XIX) represent a particular case of a radical of general formula (II) where L represents a radical of general formula (IV).

The hydrosilylation reaction is carried out in a solvent which is inert vis-à-vis hydrosilylation such as toluene, dioxan, chloroform, tetrahydrofuran or mixtures of these solvents. A metal catalyst is necessary in order to encourage the kinetics of the reaction, such as a platinum or rhodium complex. The preferred metal complex is hexachloroplatinic acid. The preferred hydrogenosilanes are bis-hydrogenosilanes such as 1,1,4,4,-tetramethyl disilyl ethylene or 1,1,3,3,-tetramethyl disiloxane. The reaction temperature varies from 50 to 180° C., the preferred temperature being 100° C.

The cross-linked polymer compounds according to the invention owe their property of insolubility in organic solvents to the fact that the cross-linking is realized between the chains of the polymers and the inter-chain bonds contain a radical of general formula (I) or (II).

The general structure of a cross-linked polymer can be represented by the general formula (VII) or (VIII) where the chiral unit symbol of general formula (IX) represents an osidic chiral unit, of a chain of a polysaccharide or oligosaccharide derivative of general formula (Xa) to (Xk), possessing ethylene radicals of general formula (XI), these latter having been subsequently reacted on themselves or with bis-thiols of general formula (XIII) or bis-hydrogenosilanes of general formula (XIV) in order to lead to the formation of radicals of general formulae (XVII), (XVIII) and (XIX), and capable of being represented by the radicals of general formulae (I) and (II).

The cross-linking between the chains of the polysaccharides derivatives, established by the subsequent insolubilization in polar organic solvents, of the said previously soluble polysaccharides derivatives, is symbolized by the fact that, in the general formulae (VII) and (VIII), the two symbols of general formula (IX) "chiral unit" are shown as belonging to a chain i and to a chain j which are separate from each other.

The novel cross-linked polymers according to the invention can be shaped as support materials by two different processes:

support materials consisting of balls containing essentially the said novel cross-linked polymers;

support materials consisting of commercial porous supports containing a percentage of less than 80% of the said novel cross-linked polymers.

Support materials consisting of balls containing essentially the said novel cross-linked polymers are obtained in two stages:

a) The polysaccharides derivatives of general formulae (Xa) to (Xk) are solubilized in a polar organic solvent such as toluene, tetrahydrofuran, dichloromethane, 1,4-dioxan or mesityl oxide, the preferred solvent being mesityl oxide. The concentration is 1 gram of derivative (Xa) to (Xk) for 10 to 50 ml of organic solvent. The preferred concentration is 1 g for 30 ml. This solution is poured onto an aqueous solution, of 10 to 200 ml, containing ionic, anionic or cationic surfactants and emulsion stabilizers of hydroxylated polymer types containing more than 16 carbon atoms.

The preferred surfactants are anionic surfactants, and among these latter sodium dodecyl sulphate. Among the hydroxylated polymers containing more than 16 carbon atoms, polyvinyl alcohols are preferred.

The concentration of sodium dodecyl sulphate varies from 0.1 to 5% by weight, the preferred concentration being 0.7% by weight. The concentration of polyvinyl alcohol varies from 0.1 to 10%, the preferred concentration being 1% for a polyvinyl alcohol having a molar mass of between 13 000 and 23 000.

The two phases are emulsified while being stirred, the speed of stirring varying from 10 to 3 000 revolutions/minute, the preferred speed being 500 revolutions/minute. The emulsion is then heated above the boiling point of the organic solvent in order to eliminate the latter, the preferred temperature being 95° C.

Balls containing essentially the polymer derivatives of formulae (Xa) to (Xk) are obtained. They have a diameter varying from 0.1 to 300 μm and their shape is more or less spherical. The diameters of preferred balls vary from 3 to 40 μm and depend on the speed of stirring of the emulsion. The specific surface area of the balls obtained varies from 1 to 600 $m^2$/g, the preferred specific surface area being from 20 to 80 $m^2$/g.

b) Balls containing essentially polysaccharides derivatives of general formulae (Xa) to (Xk) are suspended in organic or aqueous solvents in which they are insoluble, such as water, linear or branched alkanes or alcohols. The preferred organic solvents are hexane and heptane. The concentration of balls in the said polysaccharides derivatives varies from 1/2 to 1/1000 weight/volume, the preferred concentration being 1/10. The cross-linking agent is then added with solvent reflux. It is chosen from among the compounds of general formulae (XIII) or (XIV), the preferred cross-linking agents being ethane-dithiol, butane-dithiol, 1,1,4,4,-tetramethyl disilyl ethylene or 1,1,3,3-tetramethyl disiloxane.

The addition of a free radical initiator as cross-linking agent is necessary in order to obtain the cross-linked compounds of general formula (I). The quantity of free radical initiator varies from 0.1 to 5% by weight relative to the starting weight of the balls, the preferred quantity being 1%.

The quantity of compounds of general formulae (XIII) or (XIV), calculated on the number of radicals of general formula (XI) bearing reactive ethylene double bonds contained in the compounds of formulae (Xa) to (Xk), can vary from stoichiometry to 10 times stoichiometry, the preferred quantity being that corresponding to 4 times stoichiometry.

The preferred free radical initiator is benzoyl peroxide. The use of compounds of general formula (XIII) also necessitates the use of a free radical initiator in order to encourage the anti-Markovnikov addition. The quantity of free radical-initiator varies from 0.1 to 5% by weight of the quantity of compound of formula (XIII) used, the preferred quantity being 1%. The preferred free radical initiator is benzoyl peroxide. The reaction temperature varies from 30 to 100° C., the preferred temperature being 80° C. The reaction lasts for from 12 hours to 5 days, the preferred duration being 24 hours.

The suspension is filtered then washed with a ratio of 1/1 to 1/100 (weight/volume), preferably 1 g per 10 ml in a polar organic solvent in which the polysaccharides derivatives of general formulae (Xa) to (Xk) are soluble. The preferred solvent is tetrahydrofuran. The non-cross-linked compounds (Xa) to (Xk) are thus eliminated.

Support materials are obtained which consist of balls containing essentially the said novel cross-linked polymers.

Support materials consisting of commercial porous supports containing a percentage of less than 80% of novel cross-linked polymers can be obtained as follows.

a) The polysaccharides derivatives of general formulae (Xa) to (Xk) are solubilized in a polar organic solvent, such as toluene, tetrahydrofuran, dichloromethane or 1,4-dioxan, the preferred solvent being tetrahydrofuran. The concentration is 1 gram of compound (Xa) to (Xk) for 10 to 50 ml of organic solvent, the preferred concentration being 1 g in 30 ml. A commercial porous support in the form of a powdery solid is added. Its particle diameter varies from 1 to 300 μm, the preferred diameter being between 3 and 30 μm. Its pore diameter varies from 30 to 10 000 Å, the preferred diameter being 300 Å. The chemical nature of the porous support is variable and can be mineral or organic, such as silica gel, alumina, zirconia, carbon, divinylbenzene polystyrene or polyacrylamides. The preferred support is silica gel. The quantity of compound of general formulae (Xa) to (Xk) relative to the quantity of support varies from 1 to 80%, the preferred quantity being 20%. The suspension obtained is then evaporated under vacuum or at normal pressure, at a temperature of 20 to 150° C., the preferred temperature being 80° C.

b) The porous supports containing a percentage of less than 80% of compounds of general formulae (Xa) to (Xk) are suspended in organic or aqueous solvents characterized in that they do not solubilize the compounds of general formulae (Xa) to (Xk). These solvents may be, for example, water, linear or branched alkanes or alcohols. The preferred organic solvents are hexane and heptane. The quantity of solvent relative to the weight of porous support containing the compounds of general formulae (Xa) to (Xk) is from 1 times to 100 times by volume relative to the support weight. The preferred quantity is 10 times. The cross-linking agent is then added with solvent reflux. It is chosen from among the compounds of general dithiol, 1,1,3,3-tetramethy disiloxane or 1,1,4,4-tetramethyl disilyl ethylene.

The addition of a free radical initiator as cross-linking agent is necessary in order to obtain the compounds of general formula (I). The quantity of free radical initiator varies from 0.1 to 5% by weight relative to the weight of compound of general formulae (Xa) to (Xk), the preferred quantity being 1%.

The quantity of compounds of-general formulae (XIII) or (XIV), calculated on the number of radicals of general formula (XI) carrying reactive ethylene double bonds contained in the compounds of general formulae (Xa) to (Xk), can vary from stoichiometry to 10 times stoichiometry, the preferred quantity corresponding to 4 times stoichiometry. The use of compounds of general formula (XIV) requires the use of a metal catalyst the quantity of which varies from 0.05 to 1% by weight relative to the weight of compound of general formula (XIV). The preferred quantity is 0.2%, and the preferred metal catalyst is hexachloroplatinic acid.

The reaction suspension is heated to between 30 and 150° C., the preferred temperature being 80° C. The reactions lasts for from 12 hours to 5 days, the preferred duration being 24 hours.

The suspension is filtered then washed with a ratio of 1/1 to 1/100 (weight/volume), preferably about 1 g per 10 ml in a polar organic solvent in which the polysaccharides derivatives of formulae (Xa) to (Xk) are soluble. The preferred solvent is tetrahydrofuran. The non-cross-linked compounds (Xa) to (Xb) are eliminated. Support materials are thus obtained which consist of commercial porous supports containing a percentage of less than 80% of compounds of general formulae (I) and (II).

The preparation of polysaccharides derivatives of general formulae (Xa) to (Xk) is known per se and has been described by, for example, Oliveros in Application WO-A-95/18 833.

Polysaccharides are esterified and carbamates and thiocarbonates of polysaccharides obtained respectively by reacting polysaccharides with chlorides of acids, isocyanates and isothiocyanates.

An inert solvent which does not react with chlorides of acids and isocyanates is used. The reaction is generally carried out in the presence of a catalyst such as a tertiary amine, for example 4-(N,N-dimethyl amino)pyridine, in the esterification reaction, and a Lewis base, for example a tertiary amine, or a Lewis acid, for example a derivative of tin such as dibutyltin dilaurate, in the case of the reaction for obtaining carbamates and thiocarbamates.

A preferred method of obtaining these involves carrying out the esterification or carbamate-obtaining reaction in a tertiary-base type organic solvent such as pyridine or quinoline. Preferred chlorides of acids or isocyanates contain aryl groups, of the phenyl type in particular, and can be substituted, the preferred substituents being halogens, and methylene or ethylene groups.

The following examples illustrate the present invention but in no way limit it.

EXAMPLE 1

0.5 g of native cellulose (marketed by the company Merck), containing 3.1 mM of glucose units, is suspended in 15 cm$^3$ of toluene. After dehydration of the cellulose by azeotropic distillation until dry, 40 cm$^3$ of pyridine are added. After distillation of 15 cm$^3$ of solvent and cooling, 1.32 g of 10-undecenoyl chloride (6.5 mM) are added. The mixture is heated under reflux for 1 hour and a sample is taken, the analysis of which (C=67.55%; H=9.27%) shows that the degree of substitution is 1.8. 0.850 g of 3,5-dimethyl phenyl isocyanate (5.6 mM) is then added and the mixture is heated under reflux for a night. After hot filtration over no. 2 fritted glass, the reaction mixture is poured into 100 cm$^3$ of methanol. After filtration, the precipitate is dissolved in the minimum of pyridine. The solution is filtered over no. 2 fritted glass and the filtrate is poured into an ethanol/water mixture (1/1 by volume). After filtration and washing with methanol, a product with the following characteristics is obtained:

elemental analysis: C=68.58%; H=8.67%; N=2.12%.

degree of substitution: 1.8 (undecenoyl), 0.9 (3,5-dimethyl-phenyl carbamate).

A compound of general formula (Xd) is obtained

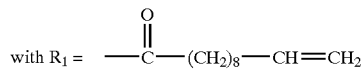

with $R_1 = -\overset{\overset{\displaystyle O}{\|}}{C}-(CH_2)_8-CH=CH_2$

-continued

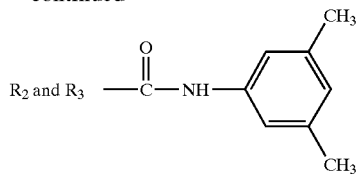

and

This compound is given the reference Xd-E1.

4 grams of compound Xd-E1 are dissolved in 80 ml of mesityl oxide. The solution obtained is kept as it is and divided into 4 parts. It is given the reference SOL(Xd-E1).

1 gram of compound Xd-E1, i.e. 20 ml of the above solution SOL(Xd-E1) is poured onto a stirred and previously prepared 0.7% by weight aqueous solution of sodium dodecyl sulphate containing 1% by weight polyvinyl alcohol having a mass of between 13 000 and 23 000. The two phases are emulsified by mechanical stirring at 500 revolutions/minute at ambient temperature for 30 minutes, then the reaction mixture is subjected to mesityl oxide reflux. The mesityl oxide is slowly distilled at normal pressure. After cooling, the suspension is filtered then washed with water. The powder is dried. The polydispersity of the balls obtained is checked by electron scanning microscopy. The size is between 1 and 22 μm with a majority between 8 and 18 μm.

The balls obtained previously are suspended in 4 ml of toluene. The reaction mixture is subjected to toluene reflux and 60 ml of ethane dithiol and 10 mg of benzoyl peroxide are added. The reflux is maintained for 24 hours. 10 mg of benzoyl peroxide are added every 3 hours. The suspension is cooled, filtered, then washed with tetrahydrofuran and ethanol. The balls are dried for 24 hours at 60° C. under vacuum.

A 100×46 mm HPLC column is then filled with these balls and the column is introduced into a HPLC system. A first test is carried out in a 90/10 heptane/isopropanol mixture. The results obtained are presented in FIG. 1.

A second test is then carried out in pure chloroform.

Test solute: 2,2,2-trifluoro-1-(9-anthryl)ethanol.

Column 100×4.6 mm

Flowrate: 1 ml/mm

U.V. detection 254 nm, To 1.2 mm

Figure 2:
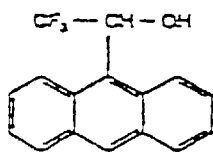
FIG. 2 depicts a result o a second test carried out in pure chloroform.
Figure 2:
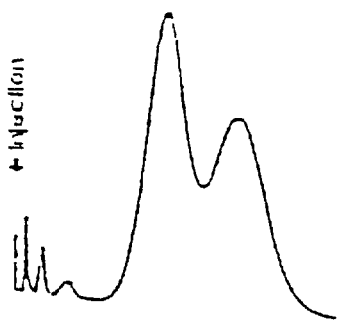

The capacity factors and the selectivity factor obtained are as follows:

$k'1=14.7-k'2=21.8-\alpha=1.5$ (see FIG. 2).

EXAMPLE 2

Figure 3:
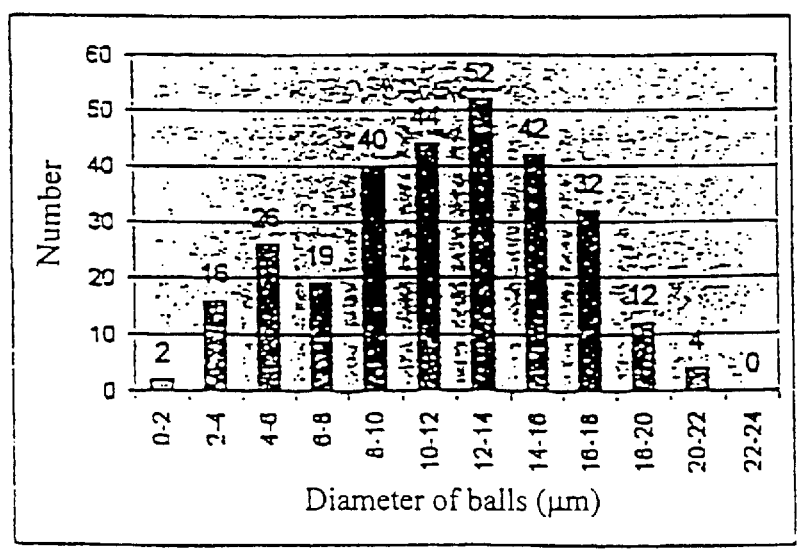
FIG. 3 depicts the distribution of balls' diameters.

20 ml of the solution of Example 1 containing 1 g of compound Xd-E1 and referenced SOL(Xd-E1) are poured onto a 1% by weight stirred aqueous sodium dodecyl sulphate solution containing 1.5% by weight polyvinyl alcohol having a mass of between 13 000 and 23 000. The two phases are emulsified by mechanical stirring at 800 revolutions/minute at ambient temperature for 30 minutes, then the reaction mixture is subjected to mesityl oxide reflux. This latter is evaporated at normal pressure. After cooling, the suspension is filtered and washed with water. The powder is dried. The diameter of the balls is measured by laser granulometry (Malvern Mastersizer Micro). The distribution of the diameters is shown in FIG. 3.

The balls obtained previously are suspended in a 50/50 toluene/heptane mixture (4 ml/4 ml). 300 mg of tetramethyl disilyl ethylene are added as well as 50 mg of hexachloroplatinic acid. The reaction mixture is refluxed for 48 hours. The suspension is cooled, filtered, then washed with tetrahydrofuran and ethanol. The balls are dried for 24 hours at 60° C. under vacuum.

Figure 4:
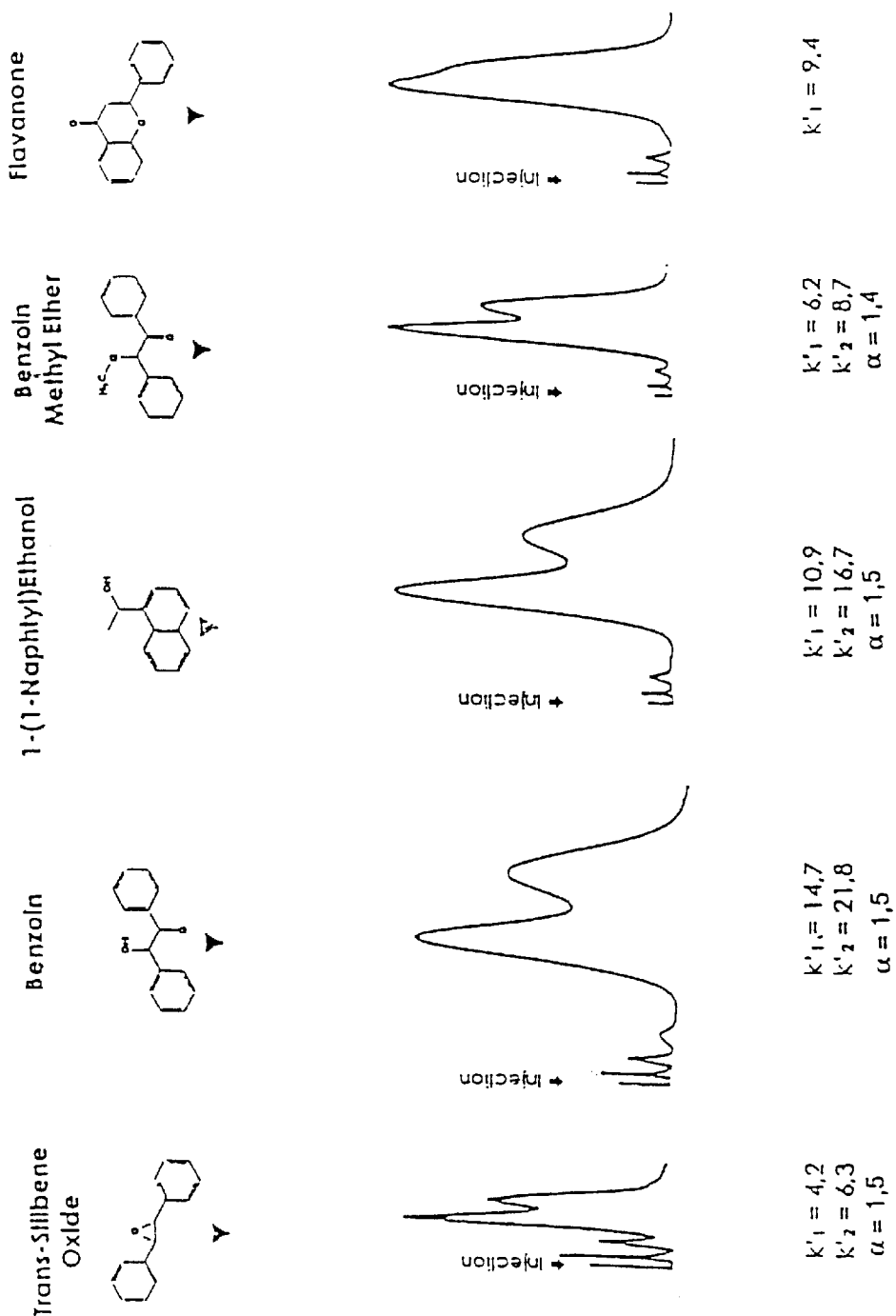
FIG. 4 depicts results of tests carried our in a 90/10/0.1 heptane/isopropanol/diethylamine mixture.

A 100×4.6 mm HPLC column is then filled with these balls and the column is introduced into a HPLC system. A first series of tests is carried out in a 90/10/0.1 heptane/isopropanol/diethylamine mixture. The results obtained are presented in FIG. 4.

A test is then carried out on indapamide in pure 1,2-dichloroethane at 80° C.

Figure 5:
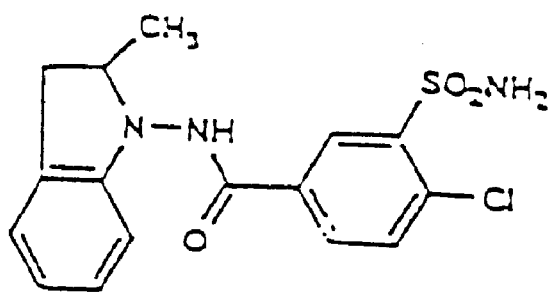
FIG. 5 depicts a result o a test carried our on indapamide in pure 1,2-dichloroethane at 80° C.
Figure 5:
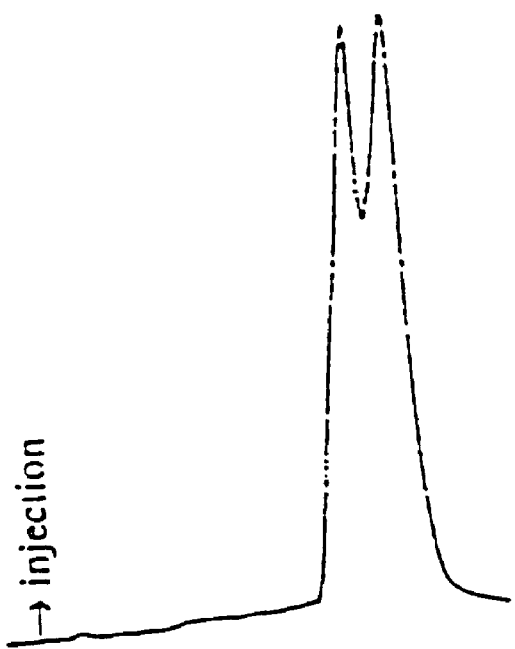

The result obtained is:

$k'1=7.3-k'2=9.7-\alpha=1.3$ (see FIG. 5)

EXAMPLE 3

20 ml of the solution of Example 1, referenced SOL(Xd-E1)and containing 1 g of compound Xd-E1, are poured onto a stirred 1% by weight aqueous sodium dodecyl sulphate solution containing 1.5% by weight polyvinyl alcohol having a mass of between 13 000 and 23 000. The two phases are emulsified by mechanical stirring at 800 revolutions/minute for 30 minutes at ambient temperature. The reaction mixture is then heated to 50° C. and the mesityl oxide evaporated under water-jet pump vacuum (between 10 and 50 mmHg). After cooling, the suspension is filtered and washed with water. The powder is dried.

The balls obtained previously are suspended in a 50/50 toluene/heptane mixture (4 ml/4 ml) and the reaction mixture is refluxed for 5 days. 10 mg of benzoyl peroxide are added every 6 hours. The suspension is filtered then washed with tetrahydrofuran and ethanol. The balls are dried for 24 hours at 60° C. under vacuum. The appearance of the balls is checked by scanning electron microscopy (SEM). The diameter of the balls ranges from 1 to 50 μm.

Figure 6:
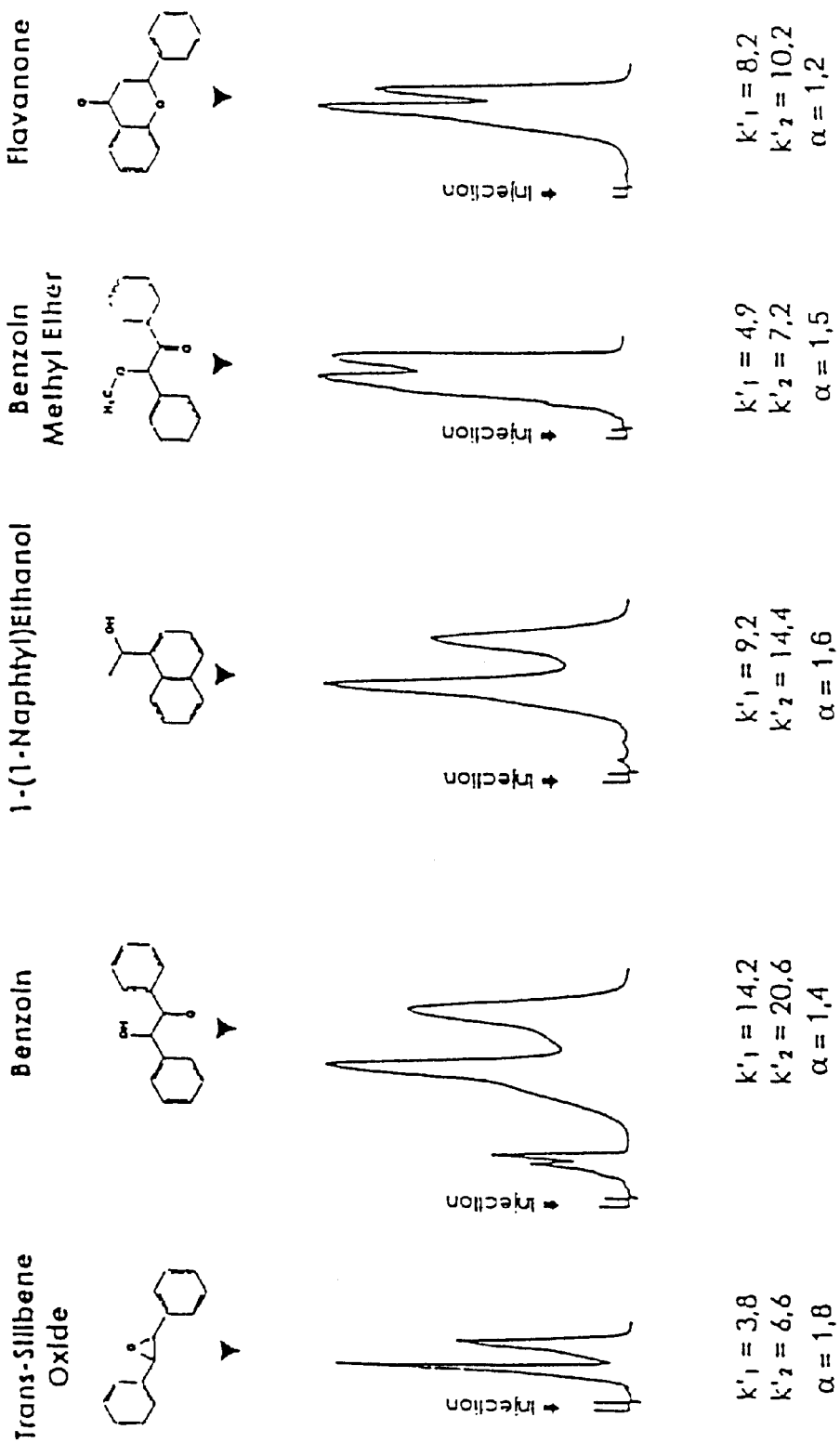
FIG. 6 depicts results of tests carried our in a 90/10 heptane/isopropanol mixture.

A 100×4.6 mm HPLC column is then filled with the balls and the column is introduced into a HPLC system. A first series of tests is carried out in a 90/10 heptane/isopropanol mixture (see FIG. 6).

Figure 7:
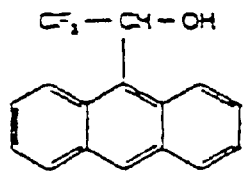
FIG. 7 depicts a result of a test carried out in pure chloroform.
Figure 7:

A second test is then carried out in pure chloroform (see results FIG. 7).

EXAMPLE 4

20 ml of the solution referenced SOL(Xd-E1) of Example 1 and corresponding to 1 g of compound Xd-E1 are stirred and 5 g of silica gel with a granulometry of 10 μm and a pore diameter of 300 Å are added. The suspension is homogenized for 1 hour at ambient temperature and the mesityl oxide is evaporated at normal pressure. The powder obtained is dried at 60° C. under vacuum. It is then taken up in 40 ml of a 50/50 heptane/toluene mixture and refluxed. 200 μl of ethane dithiol are added and the reaction mixture is refluxed for 48 hours. The suspension is filtered and washed in tetrahydrofuran then ethanol. The powder is dried (dry weight 6 g).

3 grams of the previous powder are placed in a 250×4.6 mm HPLC column and the column is introduced into a HPLC system.

The test is carried out under the following conditions:

Test solute: non-racemic 2,2,2-trifluoro-1-(9-anthryl) ethanol

Column: Xd-E1–250×4.6 mm

λ:254 nm–O.D.=0.1–Flowrate=1 ml/mn
Mobile phase: pure chloroform
Rate of advance: 2 mm/mn
The capacity factors and the selectivity rate obtained are as follows:

k'1=2.0–k'2=3.7–α=1.8

What is claimed is:

1. A cross-linked polymer compound in a three-dimensional network, comprising a radical f general formula (I) or (II)

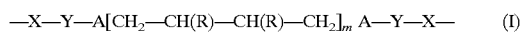  (I)

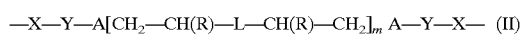  (II)

where X represents an oxygen atom of the group —NH, m is an integer other than zero equal at most to 5, R represents a hydrogen atom or a substituted or non-substituted, linear or branched alkyl radical having from 1 to 8 carbon atoms, Y represents a single bond, —NH—CO— group, —NH—CS— group or —CO— group, A represents a single bond, a linear or branched alkylene radical having from 1 to 21 carbon atoms, an arylene radical having from 6 to 18 carbon atoms or an aralkylene radical having from 7 to 40 carbon atoms, L represents a bis-thioether radical, of general formula (IIIa), bis-sulphoxide radical of general formula (IIIb), or bis-sulphone radical, of general formula (IIIc), or a bis-silane radical of general formula (IV), below:

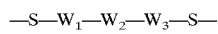  (IIIa)

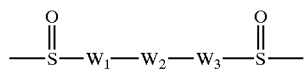  (IIIb)

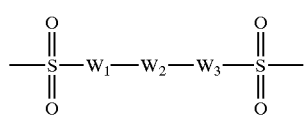  (IIIc)

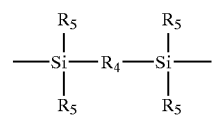  (IV)

where S represents a sulphur atom, O an oxygen atom and Si a silicon atom and where $W_1$ and $W_3$, identical or different, each represent:
   a linear or branched alkylene radical having from 1 to 21 carbon atoms, an arylene radical having from 6 to 18 carbon atoms, or an aralkylene radical having from 7 to 40 carbon atoms;

$W_2$ represents a single bond, $W_1$ an oxygen atom, a sulphur atom or a symmetrical diester of formula

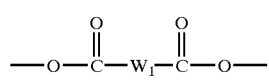  (V)

$R_5$ represents a line or branched alkyl radical having from 1 to 5 carbon atoms or hydrogen, and $R_4$ represents the radical

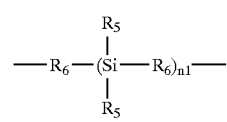  (VI)

where $R_6$ is $(CH_2)_{n2}$ or oxygen and where n1 varies from 0 to 3000 and n2 from 0 to 10, the arylene radicals contained respective in the radicals of general formulae (I) and (II) being able to be substituted by one or more atoms or radicals, identical or different, of at least one halogen atom, at least one alkyl radical containing from 1 to 4 carbon atoms, at least one alkoxy radical containing from 1 to 4 carbon atoms or at east one nitro group; wherein the radical of general formula (I) or (II) is bound to an osidic chiral unit of a linear, branched or cyclic linkage of a polysaccharide or oligosaccharide derivative according to the general formulae (VII) and (VIII):

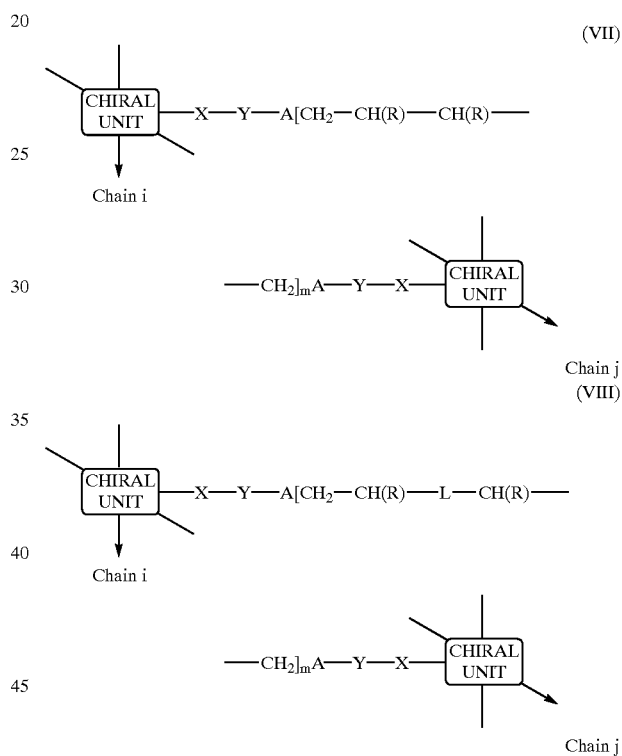

where X, Y, A, R, L and m each have the same meaning as defined above and the general formula symbol (IX)

represents an osidic chiral unit a linear, branched or cyclic linkage of a polysaccharide or oligosaccharide derivative, it being understood that "chain i" and "chain j" symbolize the fact that the chiral units at each end of the radicals of formulae (I) and (II) are situated on separate chains or separate linkages of osidic units, within the polysaccharide or the oligosaccharide.

2. A cross-linked polymer compound according to claim 1, wherein it is insoluble in polar organic solvents.

3. A cross-linked polymer compound according to claim 2, wherein osidic chiral unit of general formula (IX) corresponds to at least 1 chiral osidic unit of a polysaccharide or an oligosaccharide derivative of the general formulae (Xa) to (Xk):

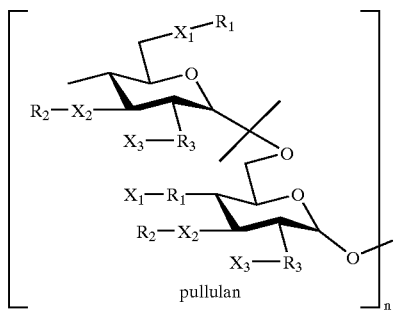
(Xa) pullulan

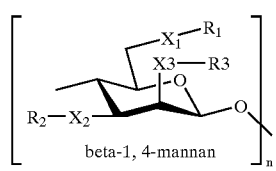
(Xb) beta-1, 4-mannan

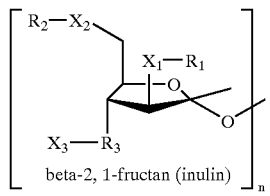
(Xc) beta-2, 1-fructan (inulin)

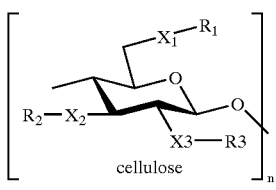
(Xd) cellulose

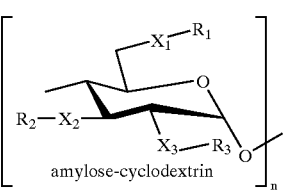
(Xe) amylose-cyclodextrin

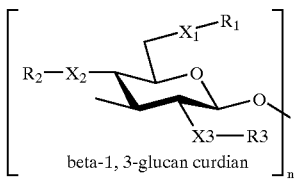
(Xf) beta-1, 3-glucan curdian

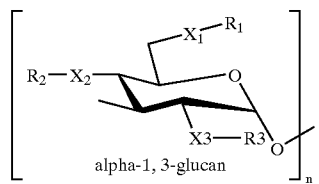
(Xg) alpha-1, 3-glucan

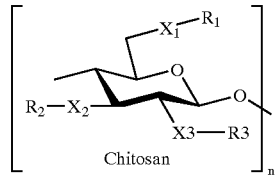
(Xh) Chitosan

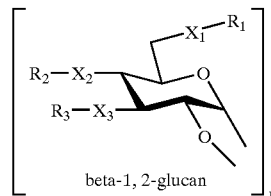
(Xi) beta-1, 2-glucan

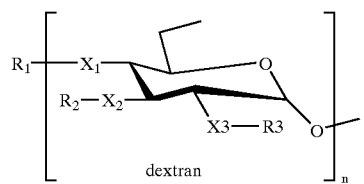
(Xj) dextran

(Xk) beta-1, 4-xylan in which:
a) the symbols $X_1$, $X_2$ an $X_3$, identical or different, each represent an oxygen atom or the group 13 NH—;
b) each of the symbols $R_1$, $R_2$ and $R_3$ independently represent:
an ethylene radical having the general formula:

$$(CH[R]\!=\!CH\!-\!)_{m1}A\!-\!Y\!-\!  \qquad (XI)$$

in which m1 is an integer other than zero equal at most to 5, R represents a hydrogen atom or a substituted or non-substituted, linear or branched alkyl radical, having from 1 to 8 carbon atoms, Y represents a single bond, —NH—CO— group, —NH—CS— group or —CO— group, A represents a single bond, a linear or branched alkylene radical having from 1 to 21 carbon atoms, an arylene radical having from to 18 carbon atoms or an arakylene radical having from 7 to 40 carbon atoms, and where X represents $X_1$, $X_2$ and $X_3$ equally;
or a radical having the formula $A_2$—$A_1$—$CX_5$—(XII) in which $X_5$ represents an oxygen or sulphur atom, $A_1$ represents a single bond or an —NH— group and $A_2$ represents an aryl radical having from 6 to 24 carbon atoms or an aralkyl radical having from 7 to 36 carbon atoms, an alkylaryl radical having from 7 to 18 carbon atoms;
or a hydrogen atom or an $NO_2$ group;

n being an integer between 5 and 20,000, it being understood that in each osidic chiral unit (Xa) to (Xk), at least one of the symbols $X_1$, $X_2$ and $X_3$ represents an oxygen atom, and that, in at least one part of the chiral osidic units constituting one of the chains of the polysaccharide derivative, at least one of the symbols $R_1$, $R_2$ and $R_3$ represents a radical of general formula (XI) and at least one of the symbols $R_1$, $R_2$ and $R_3$ represents a radical of general formula (XII).

4. A cross-linked polymer compound according to claim 3, wherein the compound of general formulae (VII) or (VIII) is obtained by reaction of a polysaccharide or oligosaccharide derivative of the general formulae (Xa) to (Xk):

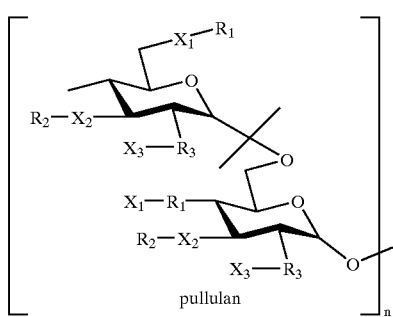

(Xa) pullulan

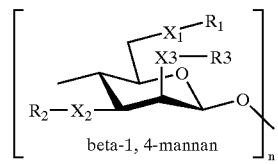

(Xb) beta-1, 4-mannan

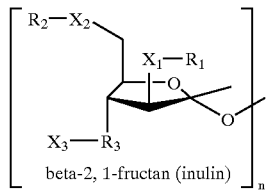

(Xc) beta-2, 1-fructan (inulin)

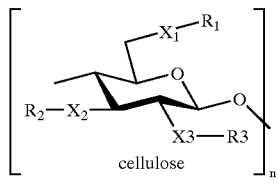

(Xd) cellulose

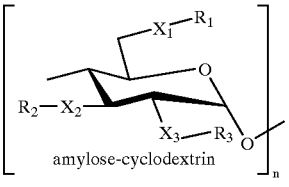

(Xe) amylose-cyclodextrin

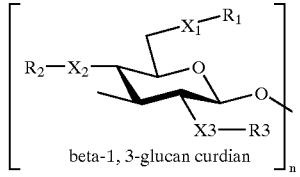

(Xf) beta-1, 3-glucan curdian

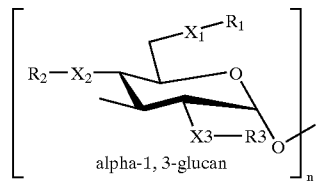

(Xg) alpha-1, 3-glucan

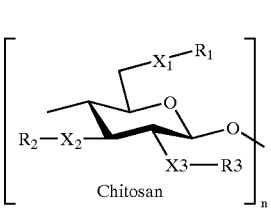

(Xh) Chitosan

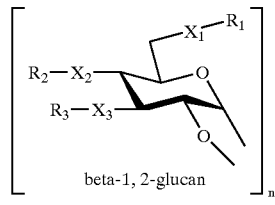

(Xi) beta-1, 2-glucan

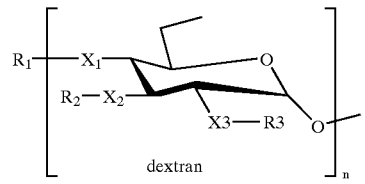

(Xj) dextran

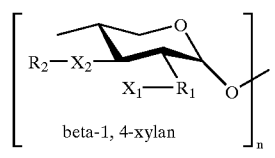

(Xk) beta-1, 4-xylan in which:
a) the symbols $X_1$, $X_2$ and $X_3$, identical or different, each represent an oxygen atom or the group —NH—;
b) each of the symbols $R_1$, $R_2$ and $R_3$ independently represent:
an ethylene radical having the general formula:

$$(CH[R]\!=\!CH\!-\!)_{m1}A\!-\!Y\!-\!  \qquad (XI)$$

in which m1 is an integer other than zero equal at most to 5, R represents a hydrogen atom or a substituted or non-substituted, linear or branched alkyl radical, having from 1 to 8 carbon atoms, Y represents a ingle bond, —NH—CO— group, —NH—CS— group or —CO— group, A represents a single bond, a linear or branched alkylene radical having from 1 to 21 carbon atoms, an arylene radical having from 6 to 18 carbon atoms or an arylene radical having from 7 to 40 carbon atoms, and where X represents $X_1$, $X_2$ and $X_3$ equally;
or a radical having the formula $A_2$—$A_1$—$CX_5$—(XII) in which $X_5$ represents an oxygen or a sulphur atom, $A_1$ represents a single bond or an —NH— group and $A_2$ represents an aryl radical having from 6 to 24 carbon atoms or an aralkyl radical having from 7 to 36 carbon atoms, an alkylaryl radical having from 7 to 18 carbon atoms;

or a hydrogen atom or an $NO_2$ group;

n being an integer between 5 and 20,000, it being understood that in each osidic chiral unit (Xa) to (Xk), at least one of the symbols $X_1$, $X_2$ and $X_3$ represents an oxygen atom, and that, in at least one part of the chiral osidic units constituting one of the chains of the polysaccharide derivative, at least one of the symbols $R_1$, $R_2$ and $R_3$ represents a radical of general formula (XI) and at least one of the symbols $R_1$, $R_2$ and $R_3$ represents a radical of general formula (XII); on itself or on a compound of general formula:

$$HS-W_1-W_2-W_3-SH \quad (XIII)$$

or

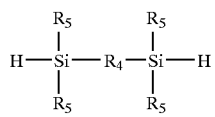

(XIV)

where S, Si, $W_1$, $W_2$, $W_3$, $R_4$ and $R_5$ have the same meaning as in claim 1.

5. A cross-linked polymer compound according to claim 4, wherein the compound of general formulae (VII) or (VIII) is obtained by reaction of an ethylene radical of general formula (XI) with the compound of general formulae (XIII) or (XIV).

6. A cross-linked polymer compound according to claim 1, wherein the osidic chiral units of general formula (IX) are situated on different chains or separate osidic linkages of a polysaccharide or oligosaccharide derivative of the general formulae (Xa) to (Xk):

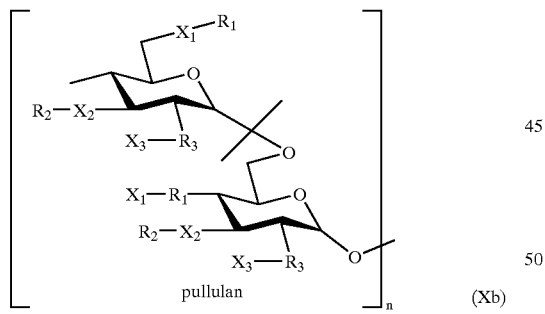

in which:

a) the symbols $X_1$, $X_2$ and $X_3$, identical or different, each represent an oxygen atom or the group —NH—;

b) each of the symbol $R_1$, $R_2$ and $R_3$ independently represent:

an ethylene radical having the general formula:

$$(CH[R]=CH-)_{m1}A-Y- \quad (XI)$$

in which m1 is an integer other than zero equal at most to 5, R represents a hydrogen atom or a substituted or non-substituted, linear or branched alkyl radical, having from 1 to 8 carbon atoms, Y represents a single bond, —NH—CO— group, —NH—CS— group or —CO— group, A represents a single bond, a linear or branched alkylene radical having from 1 to 21 carbon atoms, an arylene radical having from 6 to 18 carbon atoms or an arylene radical having from 7 to 40 carbon atoms, and where X represents $X_1$, $X_2$ and $X_3$ equally;

or a radical having the formula $A_2$—$A_1$—$CX_5$— (XII) in which $X_5$ represents an oxygen or a sulphur atom, $A_1$ represents a single bond or an —NH— group and $A_2$ represents an aryl radical having from 6 to 24 carbon atoms or an aralkyl radical having from 7 to 36 carbon atoms, an alkylaryl radical having from 7 to 18 carbon atoms;

or a hydrogen atom or an $NO_2$ group;

n being an integer between 5 and 20,000, it being understood that in each osidic chiral unit (Xa) to (Xk), at least one of the symbols $X_1$, $X_2$ and $X_3$ represents an oxygen atom, and that, in at least one part of the chiral osidic units constituting one of the chains f the polysaccharide derivative, at least one of the symbols $R_1$, $R_2$ and $R_3$ represents a radical of general formula (XI) and at least one of the symbols $R_1$, $R_2$ and $R_3$ represents a radical of general formula (XII).

7. A cross-linked polymer compound according to claim 1 wherein the radical of general formulae (IIIb) or (IIIc) is obtained by oxidation reaction of the compound containing the radical of general formula (IIIa).

8. A cross-linked polymer compound according to claim 3, wherein the osidic chiral unit of general formula (IX) corresponds to at least 1 chiral osidic unit of a polysaccharide or oligosaccharide derivative satisfying one of the general formulae (Xa) to (Xk):

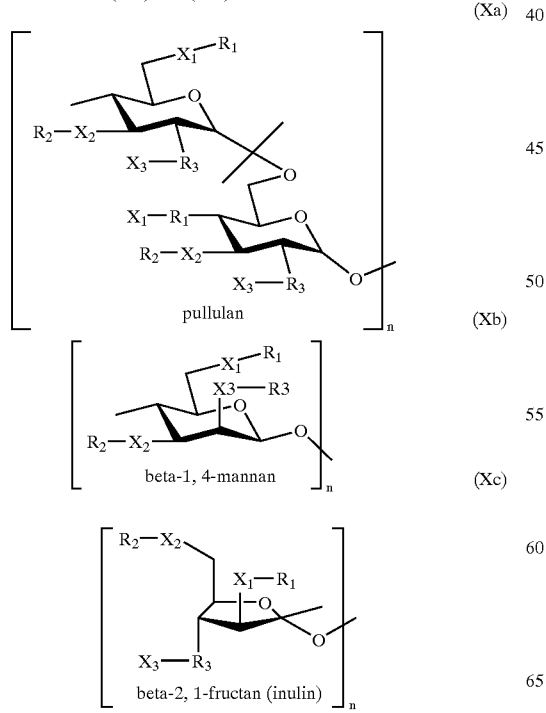

(Xa) pullulan (Xb) beta-1, 4-mannan (Xc) beta-2, 1-fructan (inulin)

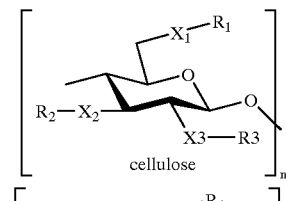

(Xd) cellulose

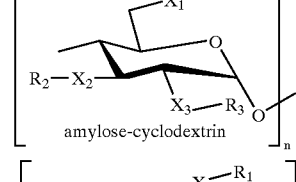

(Xe) amylose-cyclodextrin

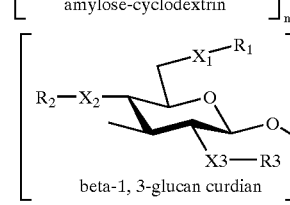

(Xf) beta-1, 3-glucan curdian

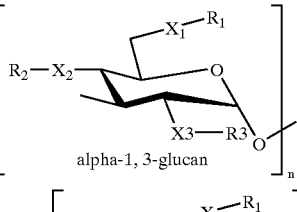

(Xg) alpha-1, 3-glucan

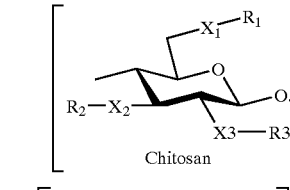

(Xh) Chitosan

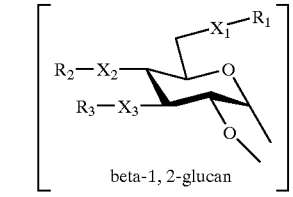

(Xi) beta-1, 2-glucan

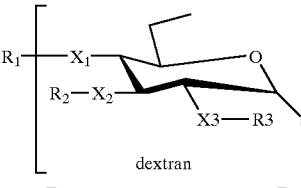

(Xj) dextran

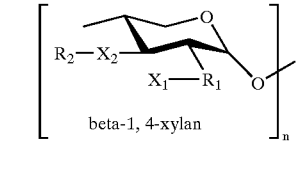

(Xk) beta-1, 4-xylan in which:
a) the symbols $X_1$, $X_2$ and $X_3$, identical or different, each represent an oxygen atom or the group —NH—;
b) each of the symbols $R_1$, $R_2$ and $R_3$ independently represent:
an ethylene radical having the general formula:

$$(CH[R]=CH-)_{m1}A-Y-\quad\quad (XI)$$

in which m1 is an integer other than zero equal at most to 5, R represents a hydrogen atom or a substituted or non-substituted, linear or branched alkyl radical, having from 1 to 8 carbon atoms, Y represents a single bond, —NH—CO— group, —NH—CS— group or —CO— group, A represents a single bond, a linear or branched alkylene radical having from 1 to 21 carbon atoms, an arylene radical having from 6 to 18 carbon atoms or an aralkylene radical having from 7 to 40 carbon atoms, or a radical having the formula $A_2$—$A_1$—$CX_5$—(XII) in which $X_5$ represents an oxygen or sulphur atom, $A_1$ represents a single bond or an —NH— group and $A_2$ represents an aryl radical having from 6 to 24 carbon atoms or an aralkyl radical having om 7 to 36 carbon atoms, an alkylaryl radical having from 7 to 18 carbon atoms;

or a hydrogen atom o an $NO_2$ group;

n being an integer between 5 and 20,000, it being understood that in each osidic chiral unit (Xa) to (Xk), at least one of the symbols $X_1$, $X_2$ and $X_3$ represents an oxygen atom, and that, in at least one part of the chiral osidic units constituting one of the chains of the polysaccharide derivative, at least one of the symbols $R_1$, $R_2$ and $R_3$ represents a radical of general formula (XI) and at least one of the symbols $R_1$, $R_2$ or $R_3$ represents a radical of general formula (XII).

* * * * *

UNITED STATES PATENT AND TRADEMARK OFFICE
CERTIFICATE OF CORRECTION

PATENT NO. : 6,677,446 B2
DATED : January 13, 2004
INVENTOR(S) : Raphael Duval

It is certified that error appears in the above-identified patent and that said Letters Patent is hereby corrected as shown below:

Column 22,
Line 44, "13" should be deleted.
Line 57, reads "from", should read -- from 6 --.

Column 24,
Line 58, reads "ingle", should read -- single --.

Column 27,
Line 58, reads "f" should read -- of --.

Column 29,
Line 11, reads "om", should read -- from --.

Column 30,
Line 1, reads "o", should read -- or --.

Signed and Sealed this

Twenty-eighth Day of June, 2005

JON W. DUDAS
*Director of the United States Patent and Trademark Office*